United States Patent [19]

Grafe et al.

[11] Patent Number: 4,973,755
[45] Date of Patent: Nov. 27, 1990

[54] STABLE SOLVENT ADDUCTS OF Z-1-(P-β-DIMETHYLAMINOETHOXY-PHENYL)-1-(P-HYDROXYPHENYL)-2-PHENYL-BUT-1-ENE

[75] Inventors: Ingomar Grafe, Nuremberg; Helmut Schickaneder, Eckental; Peter W. Jungblut, Hanover; Kurt H. Ahrens, Nuremberg, all of Fed. Rep. of Germany

[73] Assignee: Heumann Pharma GmbH & Co., Nuremberg, Fed. Rep. of Germany

[21] Appl. No.: 183,068

[22] Filed: Apr. 19, 1988

[30] Foreign Application Priority Data

Apr. 21, 1987 [EP] European Pat. Off. ........... 87105803

[51] Int. Cl.$^5$ .............................................. C07C 217/54
[52] U.S. Cl. ................................................... 564/324
[58] Field of Search ........................ 564/324; 514/648

[56] References Cited

U.S. PATENT DOCUMENTS

| | | | |
|---|---|---|---|
| 4,198,435 | 4/1980 | Richardson | 564/324 |
| 4,536,516 | 8/1985 | Harper et al. | 564/324 |
| 4,623,660 | 11/1986 | Richardson | 564/324 |

FOREIGN PATENT DOCUMENTS

| | | | |
|---|---|---|---|
| 0002097 | 5/1979 | European Pat. Off. | |
| 0054168 | 6/1982 | European Pat. Off. | 564/324 |
| 0107208 | 5/1984 | European Pat. Off. | |
| 2807599 | 8/1978 | Fed. Rep. of Germany | |
| 3239610 | 4/1984 | Fed. Rep. of Germany | 564/324 |
| 1064629 | 4/1967 | United Kingdom | 564/324 |
| 1099093 | 1/1968 | United Kingdom | |

OTHER PUBLICATIONS

P. C. Rünitz et al, J. Med. Chem., 1982, 25, 1056–1060.
P. C. Rünitz et al, Biochem. Pharmacol., 1983, 32, 2941.
Jordan et al, *J. Endocr.*, vol. 75, pp. 305–316 (1977).

*Primary Examiner*—Bruce Gray
*Attorney, Agent, or Firm*—Burns, Doane, Swecker & Mathis

[57] ABSTRACT

This invention relates to new stereochemically pure and stable adducts of Z-1-(p-β-dimethylaminoethoxyphenyl)-1-(p-hydroxyphenyl)-2-phenyl-but-1-ene and certain solvents which by virtue of their marked antioestrogenic activities may be used for the therapeutic treatment of benign breast diseases and hormone-dependent mammary tumors, in particularly by percutaneous application.

1 Claim, No Drawings

STABLE SOLVENT ADDUCTS OF Z-1-(P-β-DIMETHYLAMINOETHOXY-PHENYL)-1-(P-HYDROXYPHENYL)-2-PHENYL-BUT-1-ENE

This invention relates to new stereochemically pure and stable adducts of Z-1-(p-β-dimethylaminoethoxyphenyl)-1-(p-hydroxyphenyl)-2-phenyl-but-1-ene and certain solvents which by virtue of their marked antioestrogenic activities may be used for the therapeutic treatment of benign breast disorders and hormone-dependent mammary tumours, in particular by percutaneous application.

Tamoxifen, i.e. 1-(p-β-dimethylaminoethoxyphenyl)-1-phenyl-2-phenyl-but-1-ene, is already known from numerous publications, for example from U.S. Pat. No. 4,536,516. The said publication also describes the treatment of hormone-dependent tumours with tamoxifen.

From DE-OS No. 2 807 599 it is also known that a metabolite of tamoxifen, namely Z-1-(p-β-dimethylaminoethoxyphenyl)-1-(p-hydroxyphenyl)-2-phenyl-but-1-ene (Z-4-hydroxytamoxifen) has a more powerful antioestrogenic action than the basic molecule owing to the presence of its hydroxyl group which is important for binding to the receptor.

It has been shown, however, that the antioestrogenic activity depends on the stereochemical purity of the molecule since the E form of 4-hydroxytamoxifen acts as oestrogen (see, for example, P.C. Rünitz et al, J. Med. Chem. 25, 1056 (1982) and Biochem. Pharmacol. 32, 2941 (1983)).

According to DE-OS No. 2 807 599, Z-4-hydroxytamoxifen has a melting point of 142° to 144° C. at the time of its preparation. After a storage time of only a few weeks at room temperature, the melting point falls by about 4° C., which may be attributed to the continuous increase in the proportion of the unwanted E isomer. This Z-E isomerisation of 4-hydroxytamoxifen takes place not only in the solid substance but in particular also in solution, the 4-hydroxytamoxifen of formula I-Z isomerising to the derivative of formula I-E according to the following reaction scheme:

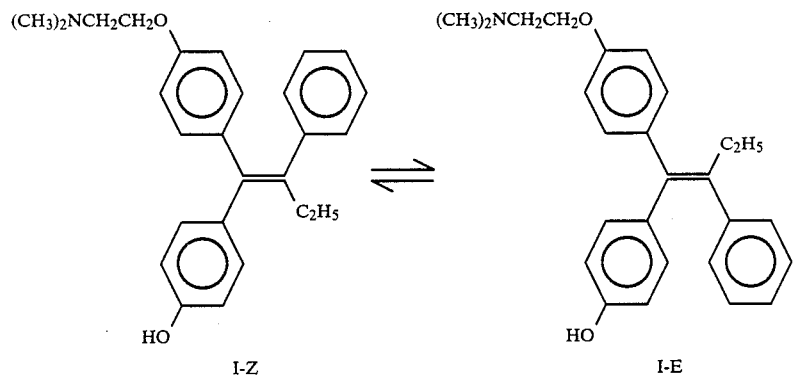

I-Z ⇌ I-E

At equilibrium, the ratio is about 3:2 in favour of the I-Z form.

As already mentioned, E-4-hydroxytamoxifen (formula I-E) behaves like pure oestrogen so that Z-4-hydroxytamoxifen preparations used for the treatment of benign breast disorders and for tumour therapy must always have an E-isomer content below 1%, no matter what form of application is employed.

This requirement cannot be fulfilled with the previously known conformationally unstable forms of Z-4-hydroxytamoxifen described in the above mentioned documents nor with the hydrohalides or alkali metal salts of the compound.

It is therefore an object of the present invention to provide stable forms of Z-4-hydroxytamoxifen. The invention is also intended to provide a convenient process for the preparation of these forms of the compound suitable for the production of large quantities.

The present invention solves this problem.

The invention relates to stable solvent adducts of Z-1-(p-β-dimethylaminoethoxyphenyl)-1-(p-hydroxyphenyl)-2-phenylbut-1-ene (Z-4-hydroxytamoxifen) corresponding to the general formula I

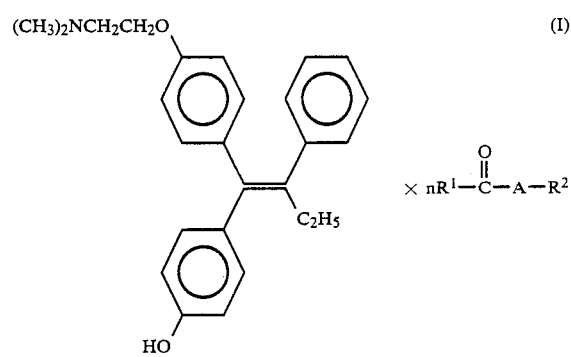

in which the part of the formula shown below:

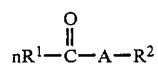

represents the solvent which according to the invention forms the adduct with Z-4-hydroxytamoxifen. In the above formula, $R^1$ denotes a hydrogen atom, a phenyl group or a $C_1$ to $C_6$ alkyl group.

The $C_1$ to $C_6$ alkyl groups may be straight chained or branched groups. Among these, both straight chained and branched $C_1$ to $C_4$ alkyl groups are preferred, especially those which are straight chained. The following are examples of such $C_1$ to $C_4$ alkyl groups: methyl, ethyl, n-propyl, i-propyl, n-butyl, i-butyl, sec.-butyl and tert.-butyl groups, the methyl and the ethyl group being particularly preferred. $R^2$ denotes a straight chained or branched $C_1$ to $C_6$ alkyl or alkenyl group, preferably a straight chained or branched $C_1$ to $C_4$ alkyl or alkenyl group, or an acyl group having up to 6 carbon atoms. Examples of suitable $C_1$ to $C_4$ alkyl groups are those already described above in the definition of $R^1$. Examples of $C_1$ to $C_4$ alkenyl groups include in particular the vinyl group and the butenyl group. Examples of acyl groups having up to 6 carbon atoms include the acetyl group and the propionyl group. The groups $R^1$ and $R^2$ may combine to form a hydrocarbon ring, for example a cyclohexyl ring. The symbol A denotes a single bond, an oxygen atom, a NH group or a carbonyl group and n has the value ½ or 1.

The following are specific examples of the solvents corresponding to the above partial formula: acetone, butanone, acetylacetone, mesityl oxide, ethyl acetate and ethyl acetoacetate, among which acetone, acetylacetone and mesityl oxide are preferred.

The solvent adducts according to the invention are conformationally stable at room temperature and under conditions of stress. They are therefore particularly suitable for use as medicaments and especially medicaments envisaged for percutaneous local application.

The adducts according to the invention are prepared by a process which includes the necessary separation of isomers. Known processes described, for example, in DE-OS No. 2 835 536 and EP-OS No. 2 097 are not suitable for the preparation of products containing less than 1% of the E isomer since the Z-E separation only takes place in the last stage of the process by repeated crystallization or by column chromatography. Although R. McCagne has already described another process in J. Chem. Res. (S) 1986, 58, it is unsuitable for the preparation of large quantities of Z-4-hydroxytamoxifen and therefore cannot be considered for practical purposes.

A suitable method of isomer separation which is convenient for the production of relatively large quantities and does not require expensive protective groups has now surprisingly been found according to the present invention. When benzoylation is carried out on a compound corresponding to the formulae II-Z and II-E

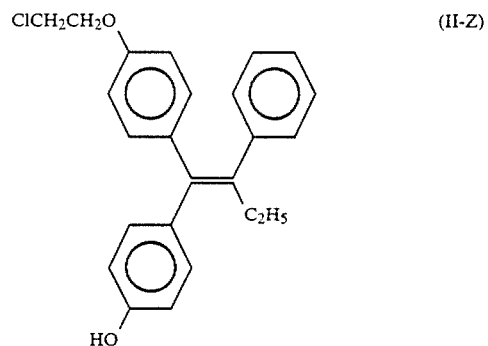

(II-Z)

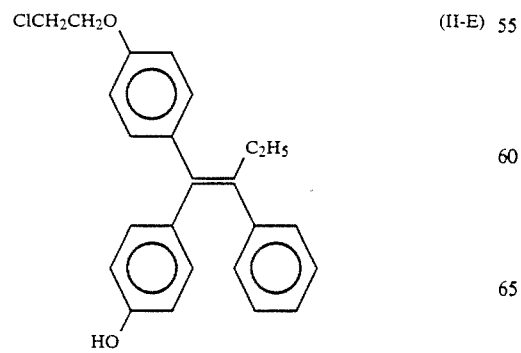

(II-E)

present as a Z-E mixture which has been prepared by known processes, an isomeric mixture is obtained as a solid product which can be separated by fractional crystallization or by kinetically controlled alcoholysis or aminolysis and the E isomer obtained can be converted into Z-4-hydroxytamoxifen.

The present invention therefore further relates to a process for the preparation of stable solvent adducts of Z-1-(p-β-dimethylaminoethoxyphenyl)-1-(p-hydroxyphenyl)-2-phenylbut-1-ene (Z-4-hydroxytamoxifen), which is characterised in that (a) an isomeric mixture corresponding to the general formulae II-Z and II-E

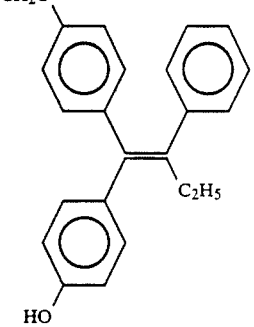

(II-Z)

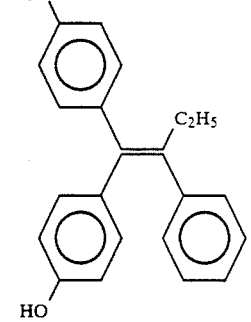

(II-E)

is reacted with an acid chloride corresponding to the general formula III

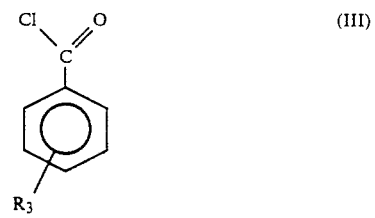

(III)

wherein $R^3$ stands for a hydrogen atom, a $C_1$ to $C_4$ alkyl group, an aryl group, a nitro group or a halogen atom to form an isomeric mixture corresponding to the general formulae IV-Z and IV-E

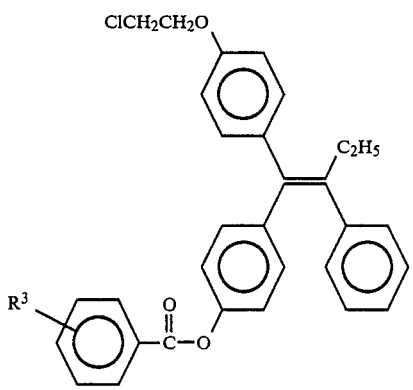
(IV-Z)

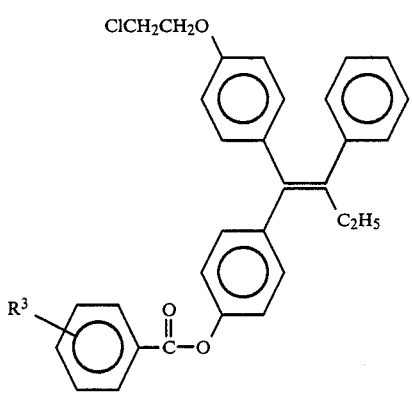
(IV-E)

(b) the IV-E isomer is separated from this isomeric mixture by fractional crystallization of the compounds IV-E and IV-Z or by kinetically controlled alcoholysis or aminolysis of the compound corresponding to the general formula IV-Z and removal of the IV-E isomer as less readily soluble component by filtration, (c) the compound of the general formula IV-E thus obtained is converted by a reaction with dimethylamine into the compound corresponding to the general formula V-Z

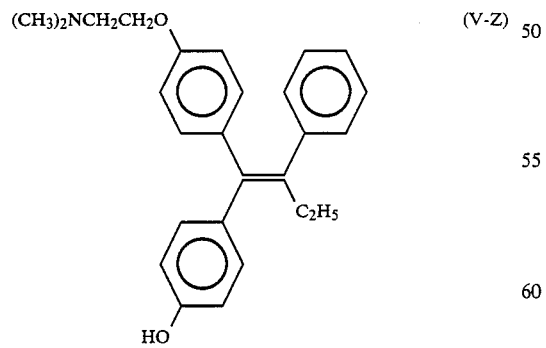
(V-Z)

(d) the compound corresponding to the general formula V-Z is converted by crystallization from a chlorinated hydrocarbon (CKW) into an adduct corresponding to the general formula VI-Z

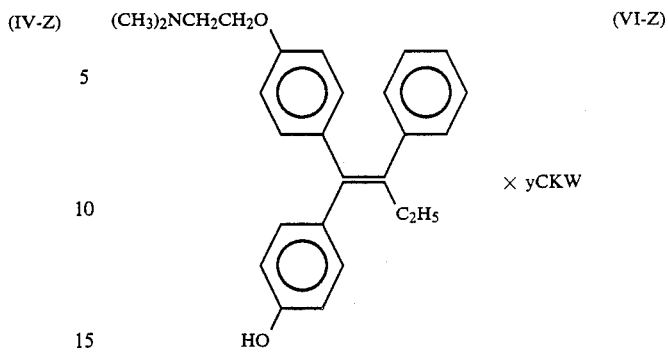
(VI-Z) × yCKW wherein y has the value $\frac{1}{2}$ to 1, and in that (e) the compound corresponding to the general formula VI-Z is converted into the stereochemically pure and stable solvent adduct of the general formula I by crystallization from a carbonyl compound corresponding to the general formula VII

(VII)

wherein $R^1$, A and $R^2$ have the meanings indicated above.

In the first stage of the process according to the invention, an isomeric mixture corresponding to the general formulae II-Z and II-E

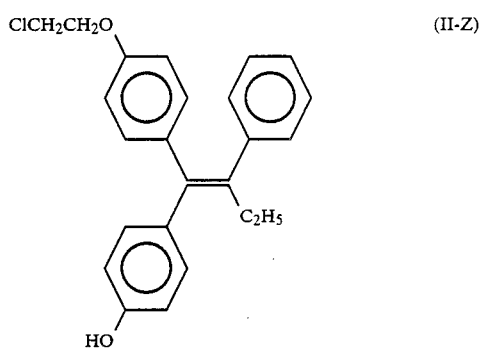
(II-Z)

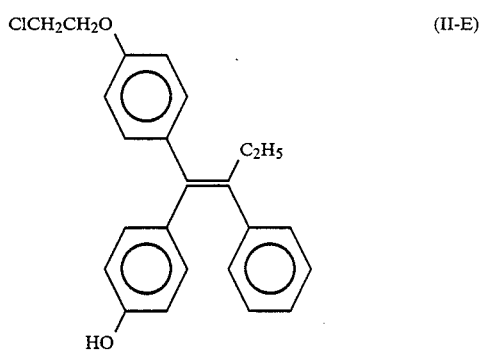
(II-E)

is reacted with an acid chloride corresponding to the general formula III

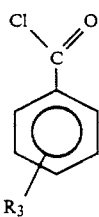

(III)

wherein R³ stands for a hydrogen atom, a $C_1$ to $C_4$ alkyl group as defined above, an aryl group, preferably a phenyl group, a nitro group or a halogen atom, for example a fluorine, chlorine or bromine atom, to form an isomeric mixture corresponding to the general formulae IV-Z and IV-E

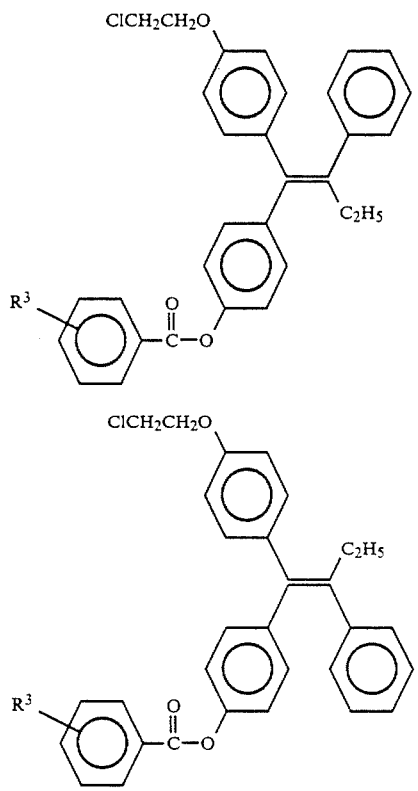

In the general formulae IV-Z and IV-E, the symbol R³ has the meanings indicated above.

The isomeric mixture of II-Z and II-E may be prepared by known processes, for example as described by R. McCagne in J. Chem. Res. (S) 1986, 58.

This stage of the process according to the invention, i.e. benzoylation, is carried out in organic solvents, for example aliphatic or aromatic hydrocarbons such as hexane or toluene. The reaction mixture may contain an agent which acts as acid acceptor, for example potash, and a phase transfer catalyst such as tetrabutyl ammonium hydrogen phosphate.

The reaction may be carried out, for example, at temperatures from −10° to 25° C., preferably from 0° to 10° C. The molar ratio of isomeric mixture to acid chloride of the general formula III is in the range of from 1.5:1 to 1:1.

Working up of the reaction mixture is carried out by known methods, e.g. evaporation of the solvent and crystallization, and the isomeric mixture is thereby obtained as a solid.

In the second stage of the process according to the invention, the isomeric mixture obtained in the first stage is either separated by the conventional method of fractional crystallization of the compounds IV-E and IV-Z or by kinetically controlled alcoholysis or aminolysis of the compound IV-Z. Fractional crystallization is carried out in known manner. Kinetically controlled alcoholysis or aminolysis of the compound IV-Z may be carried out, for example, with methanol, ethanol or isopropanol as alcohol or with piperidine, pyrrolidine or diethylamine as amine in an alcohol. The reaction is carried out at temperatures in the range from 20° C. to the boiling point of the particular alcohol used. Kinetically controlled alcoholysis or aminolysis acts only on the Z form of compound IV, which is thereby converted into the E form of compound V. This E form precipitates from the solvent while the IV-E compound remains in solution.

The E isomer of compound V may be separated by filtration.

In the third stage of the process according to the invention, the compound of the general formula IV-E is converted by a reaction with dimethylamine into the compound corresponding to the general formula V-Z

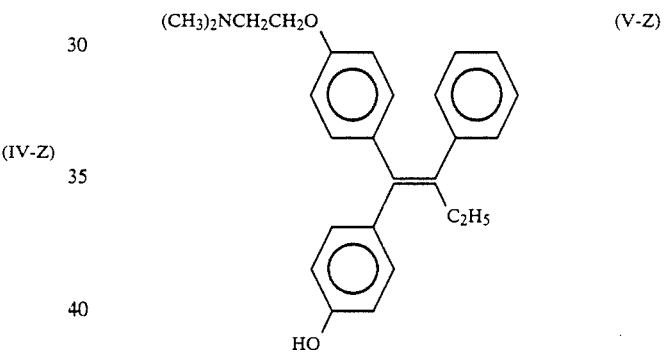

The reaction may be carried out, for example, in a mixture of water and methyl glycol. A reaction temperature of from 20° to 95° C. is employed, preferably from 85° to 95° C. The molar ratio of compound IV-E to dimethylamine is in the range of from 1:1.5 to 1:1.

In the next stage, i.e. the fourth stage of the process according to the invention, the compound corresponding to the general formula V-Z is converted by crystallization from a chlorinated hydrocarbon (CKW) into an adduct corresponding to the general formula VI-Z

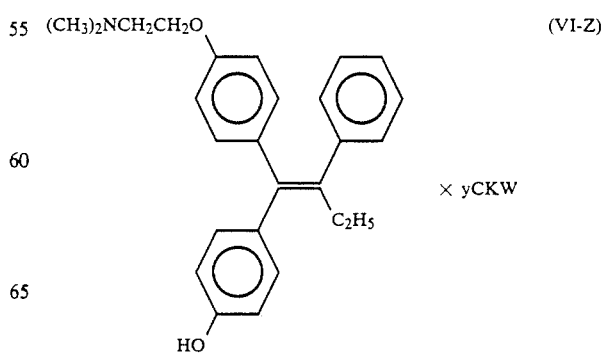

wherein y has a value from ½ to 1. Perchloroethylene, trichloroethylene or chloroform may suitably be used as chlorinated hydrocarbon. The concentration of the compound corresponding to the general formula V-Z in the chlorinated hydrocarbon may be, for example, from 1 to 50% by weight. Crystallization of the betaine is carried out in known manner by dissolving it in the chlorinated hydrocarbon at an elevated temperature and leaving the solution to cool.

The resulting adduct with the chlorinated hydrocarbon has discrete DSC maxima.

In the fifth or last stage of the process according to the invention, the compound corresponding to the general formula VI-Z is converted into the stable solvent adduct according to the invention corresponding to the general formula I by crystallization from a carbonyl compound corresponding to the general formula VII

(VII)

wherein $R^1$, $R^2$ and A have the meanings defined above. The solvent corresponding to the general formula VII may be used as a mixture with an inert, apolar solvent such as hexane. The concentration of the compound corresponding to the general formula VI-Z in the solvent may be, for example, from 1 to 50% by weight.

This stage of the process according to the invention is carried out as follows: the compound corresponding to the general formula VI-Z is dissolved in the carbonyl compound or the mixture of carbonyl compound and inert, apolar solvent at an elevated temperature, for example up to the boiling point of the solvent used, and the solution is left to cool. The solvent adduct according to the invention, which separates on cooling, may then easily be separated by filtration.

Definite maxima and the specific IR absorption bands of the carbonyl frequencies prove that the products according to the invention are stable solvent adducts. The DSC maxima of the solvent adducts of Z-4-hydroxytamoxifen according to the invention are summarized in the table below.

| Carbonyl Compound corresponding to the general formula VII | DSC Maxima (°C.) of the adducts (heating rate 2° C./min) | | IR (KBr) $v - C = 0\ (cm^{-1})$ | |
|---|---|---|---|---|
| Acetone | 78, | 138 | 1711 | |
| Butanone | 71, | 91, 146 | 1716 | |
| Acetylacetone | 123, | 133 | 1612, 1516 | |
| Mesityl oxide | 111, | 139, 159 | 1687, 1610 | |
| Ethyl acetate | 92, | 144, 148 | 1737 | |
| Ethyl acetoacetate | 92, | 130, 158 | 1735, 1715, 1650, 1630 | |

DTA Apparatus: Mettler FP 85 IR Apparatus: Perkin-Elmer, Model 1420

The distinct shift in the carbonyl frequencies of the molecules of solvent adduct from those of the free carbonyl compounds (formula VII) show that the solvent molecules are very firmly bound in the crystal.

As already mentioned, the solvent adducts according to the invention are particularly suitable for the preparation of medicaments by virtue of the stability of their conformation. In particular, they are suitable for the preparation of medicaments for percutaneous local application.

The invention therefore also relates to medicaments which contain at least one stable solvent adduct of the type described above as active ingredient as well as conventional carriers and auxiliary substances.

The following pharmaceutical auxiliary agents and carriers are particularly suitable for the preparation of medicaments for percutaneous application: water miscible solvents such as ethanol, isopropyl alcohol, propylene glycol, dimethyl sulphoxide, dimethyl formamide and tetrahydrofuran, used singly or as mixtures, preferably together with 50% of water. Such solutions may be applied in suitable doses, either directly or in the form of ointments or creams. Suitable auxiliary substances for ointments or creams, in which the active ingredient is either dissolved or suspended, include fatty acid esters such as ethyl stearate, isopropyl myristate, isopropyl palmitate, oleic acid oleyl ester, caprylic/caproic acid esters of saturated fatty alcohols with chain lengths of $C_8$ to $C_{12}$, etc., triglycerides such as caprylic/caproic acid triglyceride, mixtures of triglycerides with vegetable fatty acids having chain lengths of from $C_8$ to $C_{12}$, etc., fatty alcohols such as cetyl stearyl alcohol or oleyl alcohol; fatty acids such as oleic acid and stearic acid; surface active agents, e.g. non-ionogenic agents such as polyoxyethylated sorbitanmonooleate, glycerol monostearate or polyoxyethylene stearate, cation active agents such as cetyl trimethyl ammonium chloride and anion active agents such as sodium lauryl sulphate or fatty alcohol ether sulphate; ampholytic agents such as lecithin; stabilizers such as highly disperse silicon dioxide, montmorillonites, and antioxidants such as tocopherols and butylhydroxy anisole.

The medicaments according to the invention contain from about $10^{-8}$ g to about 0.2 g of solvent adduct of Z-4-hydroxytamoxifen per unit dose. Contents of $10^{-6}$ g to 0.1 g are preferred. A unit dose of the medicament according to the invention contains from $10^{-8}$ g to 0.2 g, preferably from 0.01 g to 0.2 g, of the solvent adduct according to the invention. The unit dose may be administered once or several times daily.

It may be necessary in some cases to deviate from the quantities indicated, in particular according to the individual patient's response to the active ingredient proposed according to the invention, the patient's condition and similar factors. There are cases, for example, where less than the minimum quantity indicated above may be sufficient while in other cases it is necessary to exceed the upper limit indicated.

The invention will now be illustrated by examples.

EXAMPLE 1

Preparation of a Complex of Z-4-Hydroxytamoxifen with a chlorinated hydrocarbon.

(a) Preparation of Z-E-1-(4-Benzoyloxyphenyl)-1-[(2-chloroethoxy)-phenyl]-2-phenylbutene-(1).

A hydrochloric acid solution of 1-[4-(2-chloroethoxy)phenyl]-1-(4-hydroxyphenyl)-2-phenylbutene prepared according to R. McCagne, J. Chem. Res. (S) 1986, 58 in a batch of 0.5 mol is concentrated by evaporation under vacuum and subjected to steam distillation until no more organic compounds distil over.

The organic compound is taken up with 300 ml of toluene. Phase separation is carried out and the organic phase is added to a mixture of 0.6 mol of potash in 250 ml of water and 3 ml of 50% tetrabutyl ammonium hydrogen phosphate.

0.75 mol of benzoyl chloride is added dropwise with stirring over a period of half an hour at a temperature of at most 40° C. and stirring is continued at 20° to 30° C. until no more $CO_2$ evolves. After phase separation, the solvent is evaporated off and the residue (260 g) is taken up with 260 ml of n-butanol.

This solution is added dropwise to 1 liter of methanol at 0° to 10° C. over a period of about 8 to 16 hours so that slow crystallization prevents the formation of lumps. The mixture is then left to stand for at least 24 hours at 0° C. and suction filtered and washed with methanol. The product may then be dried under a vacuum at 50° C.

Yield: 122 g (Z-E mixture)=51% of theoretical.
DSC max=107°+109° C. (2° C./min)
$^1$H-NMR data (CDCl$_3$): 0.95 t (3H), 2.5 q (2H), 3.7 m (2H), 4.1 t (1H), 4.2 t (1H), 6.6–8.3 m (18H) ppm.

(b) Z-E Separation of the Olefines from (a)

0.2 mol of the Z-E mixture from (a) are boiled under reflux with 0.1 mol of piperidine in 500 ml of methanol for 3 hours and suction filtered at 50° C. The product is washed with 100 ml of methanol.

Yield: 14 g of E-1-(4-benzoyloxyphenyl)-1-[4-(2-chloroethoxy)phenyl]-2-phenylbutene-(1).
Content >90%
DSC max=133° C. (2° C./min)
$^1$H-NMR data (CDCl$_3$): 0.95 t (3H), 2.5 q (2H), 3.8 t (2H), 4.25 t (2H), 7–8.3 m (18H) ppm.

(c$_1$) Preparation of Z-4-Hydroxytamoxifen-chloroform Complex 0.3 mol of the E isomer of the benzoyl compound from (b) are dissolved in 0.3 liters of glycol, 0.2 liters of methyl glycol and 50 ml of 40% dimethylamine at 85° C. 100 ml of 40% dimethylamine are added dropwise over a period of 3 hours, during which hardly any amine escapes. The reaction mixture is then heated to 95° C. and the excess amine is driven off with a stream of nitrogen. After the addition of 200 ml of water, the pH is adjusted to approximately 3 with 30% sulphuric acid and the mixture is extracted with a mixture of 150 ml of toluene and 50 ml of special grade petroleum spirit at 30° C. After the addition of 50 g of common salt, the aqueous phase is extracted twice with 200 ml portions of methylene chloride and the combined organic phases are washed with a 5% sodium chloride solution and with dilute ammonia. The solvent is evaporated off and the residue (170 g) is crystallized from 0.5 l of chloroform. The product is suction filtered after 24 hours.

Yield: 106 g.
$C_{27}H_{30}Cl_3NO_2$ (molecular weight 506.88)=69% of theoretical.

DSC max=104°–138° C. (2° C./min)

(c$_2$) Preparation of Z-4-Hydroxytamoxifen-perchloroethylene Complex.

The procedure is the same as in (c$_1$) but with crystallization from perchloroethylene.

Yield: 117 g.
$C_{28}H_{29}Cl_4NO_2$ (mol. wt. 553.33)=71% of theoretical.
DSC max=135° C. (2° C./min)

EXAMPLE 2

Preparation of Z-4-Hydroxytamoxifen-acetone Complex 0.1 mol of the chloroform or perchloroethylene complex of Z-4-hydroxytamoxifen from Examples (1c$_1$) and (1c$_2$) are recrystallized from 300 ml of acetone and suction filtered at 10° C.

Yield: 36 g.
$C_{32}H_{41}NO_4$ (mol. wt. 445.58)=81% of theoretical.

EXAMPLE 3

Preparation of the Z-4-Hydroxytamoxifen-mesityl oxide complex.

0.1 mol of the 4-hydroxytamoxifen complexes from Examples (1c$_2$) and 2 are introduced into 400 ml of mesityl oxide at 60° C. When the substance has dissolved, the solution is cooled to 15° C. and the precipitate obtained is suction filtered and washed with 75 ml of methyl tert.-butyl ether.

Yield: 34.5 g=79% of theoretical.
Composition: $2 \times C_{26}H_{29}NO_2 \times C_6H_{10}O$
Analysis: calculated: C 79.77; H 7.86; N 3.21 found: C 80.00; H 7.79; N 3.22
$^1$H-NMR data (CDCl$_3$): 0.9 t (6H), 1.9 s (3H), 2.05 s (6H) 4 J 1 Hz, 2.15 s (12H), 2.5 m (8H), 3.9 t (4H), 6.15 s broad (1H), 6.5–7.3 m (26H) ppm.

There is no indication of the presence of the structurally isomeric E-4-hydroxytamoxifen.

We claim:

1. A stable solvent adduct of Z-1-(p-β-dimethylaminoethoxyphenyl)-1-(p-hydroxyphenyl)-2-phenyl-but-1-ene corresponding to the formula:

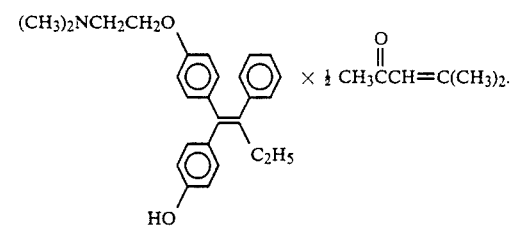

* * * * *